US012281969B1

(12) United States Patent
Alsayegh et al.

(10) Patent No.: US 12,281,969 B1
(45) Date of Patent: Apr. 22, 2025

(54) SOIL LAYER EXTRACTOR TOOL FOR SYSTEM OF OBSERVING SOIL SAMPLES

(71) Applicant: KUWAIT UNIVERSITY, Safat (KW)

(72) Inventors: Naser Alsayegh, Safat (KW); Fatemah M. Safar, Safat (KW); Shikha A. Ebrahim, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 18/979,051

(22) Filed: Dec. 12, 2024

(51) Int. Cl.
G01N 1/08 (2006.01)
G01N 33/24 (2006.01)

(52) U.S. Cl.
CPC ............. *G01N 1/08* (2013.01); *G01N 33/24* (2013.01)

(58) Field of Classification Search
CPC .......... G01N 1/08; G01N 1/40; G01N 1/4055; G01N 33/24
See application file for complete search history.

(56) References Cited

U.S. PATENT DOCUMENTS

| 4,556,114 A | 12/1985 | Ryan |
| 4,653,336 A | 3/1987 | Vollweiler |
| 4,804,050 A * | 2/1989 | Kerfoot .................. E21B 7/26 175/21 |
| 4,848,484 A | 7/1989 | Clements |
| 5,337,620 A * | 8/1994 | Kalidini .................. G01N 1/08 73/864.64 |
| 6,330,921 B1 * | 12/2001 | Barber .................. A01B 1/165 D8/7 |
| 6,339,966 B1 | 1/2002 | Kalidini |
| 6,393,926 B1 * | 5/2002 | Bowersox, Jr. ....... B01L 3/0217 73/864.64 |

FOREIGN PATENT DOCUMENTS

| CN | 104251786 A | 12/2014 | |
| CN | 204116337 U | 1/2015 | |
| CN | 207570823 U | 7/2018 | |
| CN | 108426734 A * | 8/2018 | ............. G01N 1/08 |
| CN | 207908246 U * | 9/2018 | |

(Continued)

OTHER PUBLICATIONS

Machine Translation of CN-108426734-A (Year: 2018).*

(Continued)

*Primary Examiner* — Nguyen Q. Ha
(74) *Attorney, Agent, or Firm* — Nath, Goldberg & Meyer; Joshua B. Goldberg

(57) ABSTRACT

A soil layer extractor tool used in a system for obtaining a soil sample, dispensing liquid into the soil sample, collecting the resulting leachate, and extracting a soil layer from the obtained soil sample. The soil layer extractor tool includes a base, a holder for a sample tube, and crane for lifting walls of the sample tube to expose a soil sample within the sample tube. The base includes a lower base portion and upper base portion joined in sliding relation. Vertical posts are mounted on the upper base portion, and extractor blades are mounted on the vertical posts for extracting a soil layer. The extractor blades include a lower blade and upper blade, and a vertical blade positioned therebetween. A soil layer is extracted by a sliding movement pushing the extractor blades into the exposed soil sample thus removing a soil layer from sample contained in the sample tube.

15 Claims, 11 Drawing Sheets

(56) References Cited

FOREIGN PATENT DOCUMENTS

| | | |
|---|---|---|
| CN | 110133230 A | 8/2019 |
| CN | 112433035 A | 3/2021 |
| CN | 215525140 U | 1/2022 |
| CN | 114397137 A | 4/2022 |
| CN | 216209121 U | 4/2022 |
| CN | 115615744 A | 1/2023 |
| CN | 218349833 U | 1/2023 |
| CN | 218567395 U | 3/2023 |
| CN | 113970506 B | 10/2023 |

OTHER PUBLICATIONS

Machine Translation of CN-207908246-U (Year: 2018).*

Ferreira, Francisca TSM, et al. "Improved sequential injection method for phosphate quantification within a wide dynamic range with in-line pre-concentration to monitor soil leachates." Talanta Open 2 (2020): 100015.

* cited by examiner

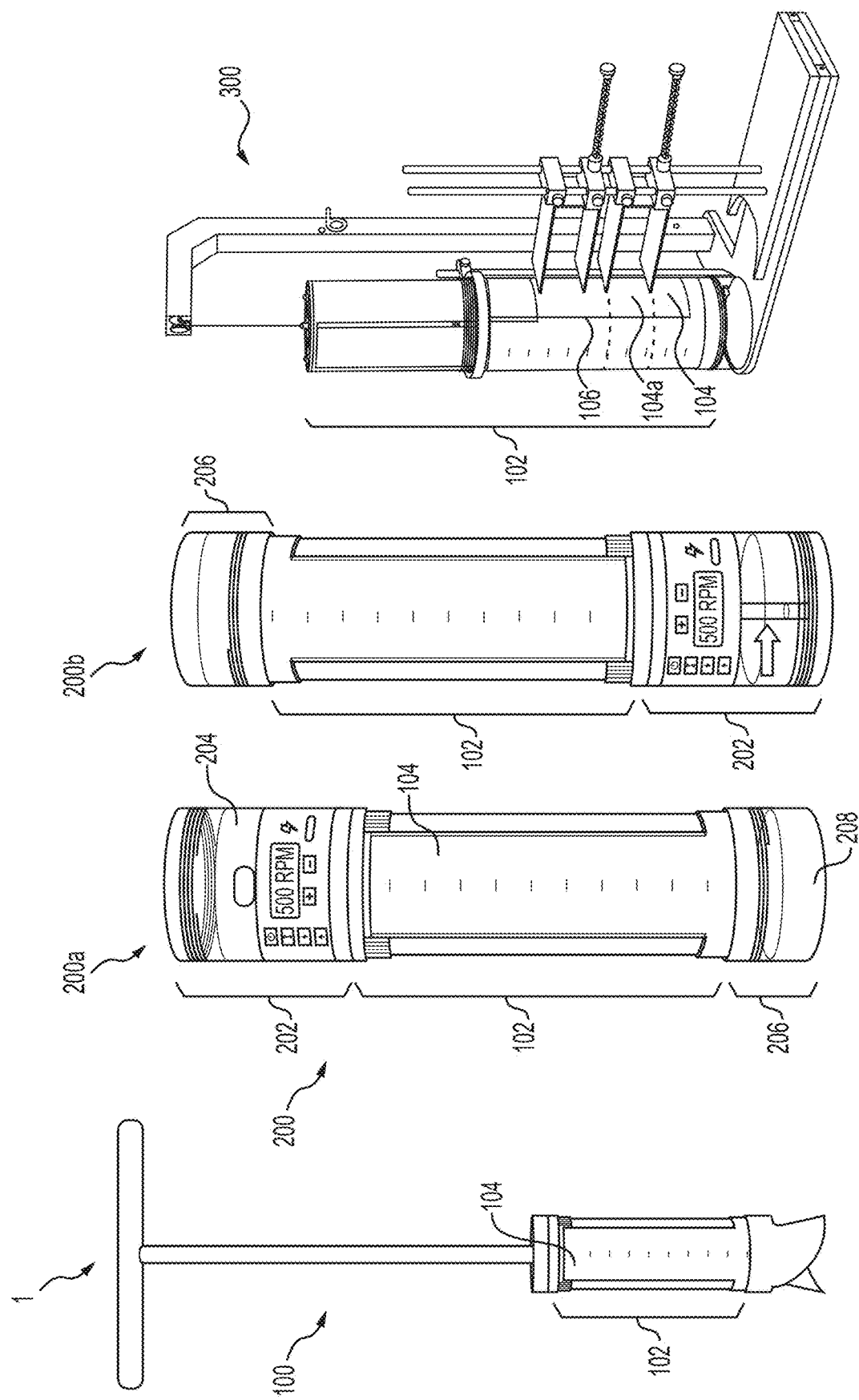

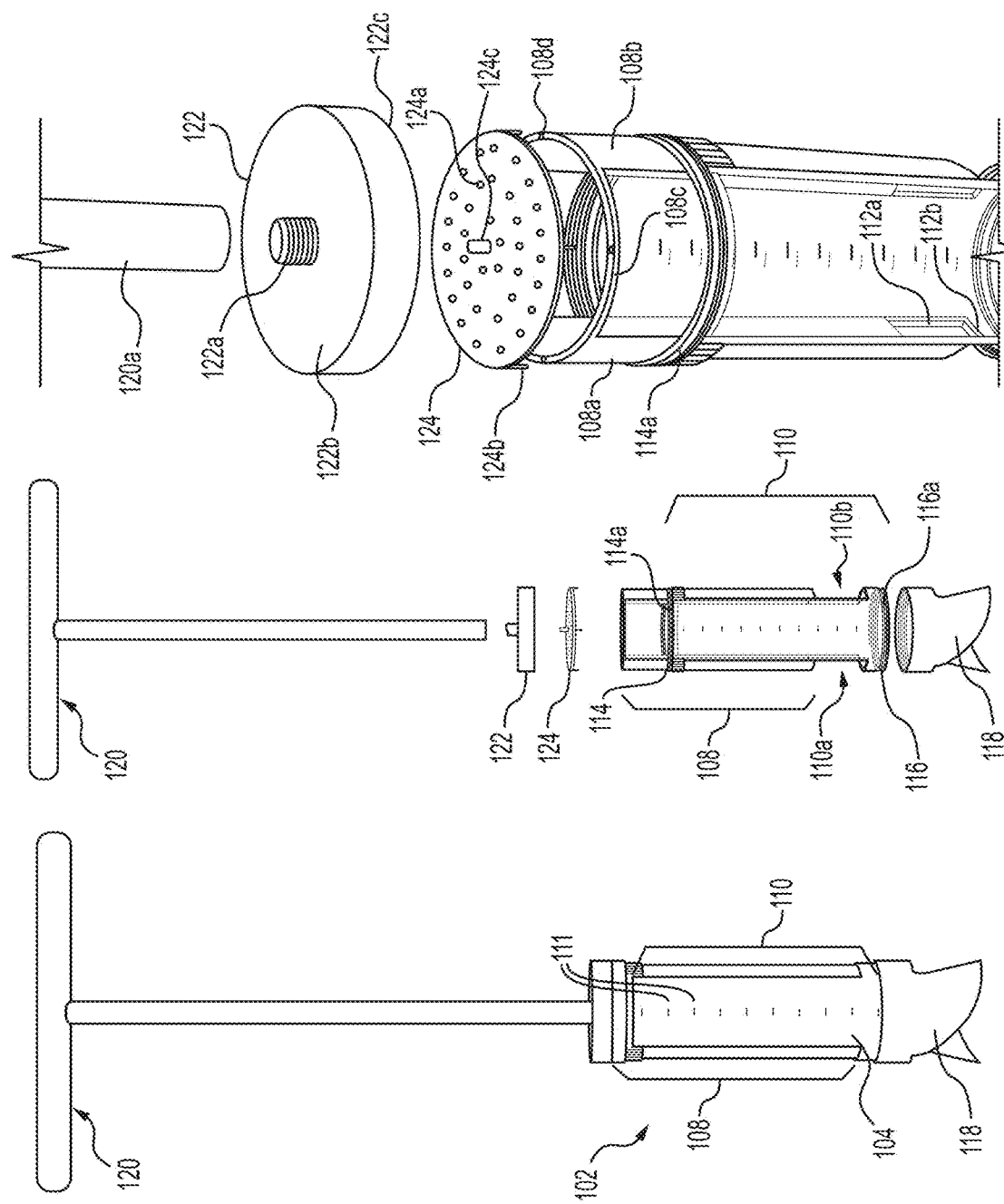

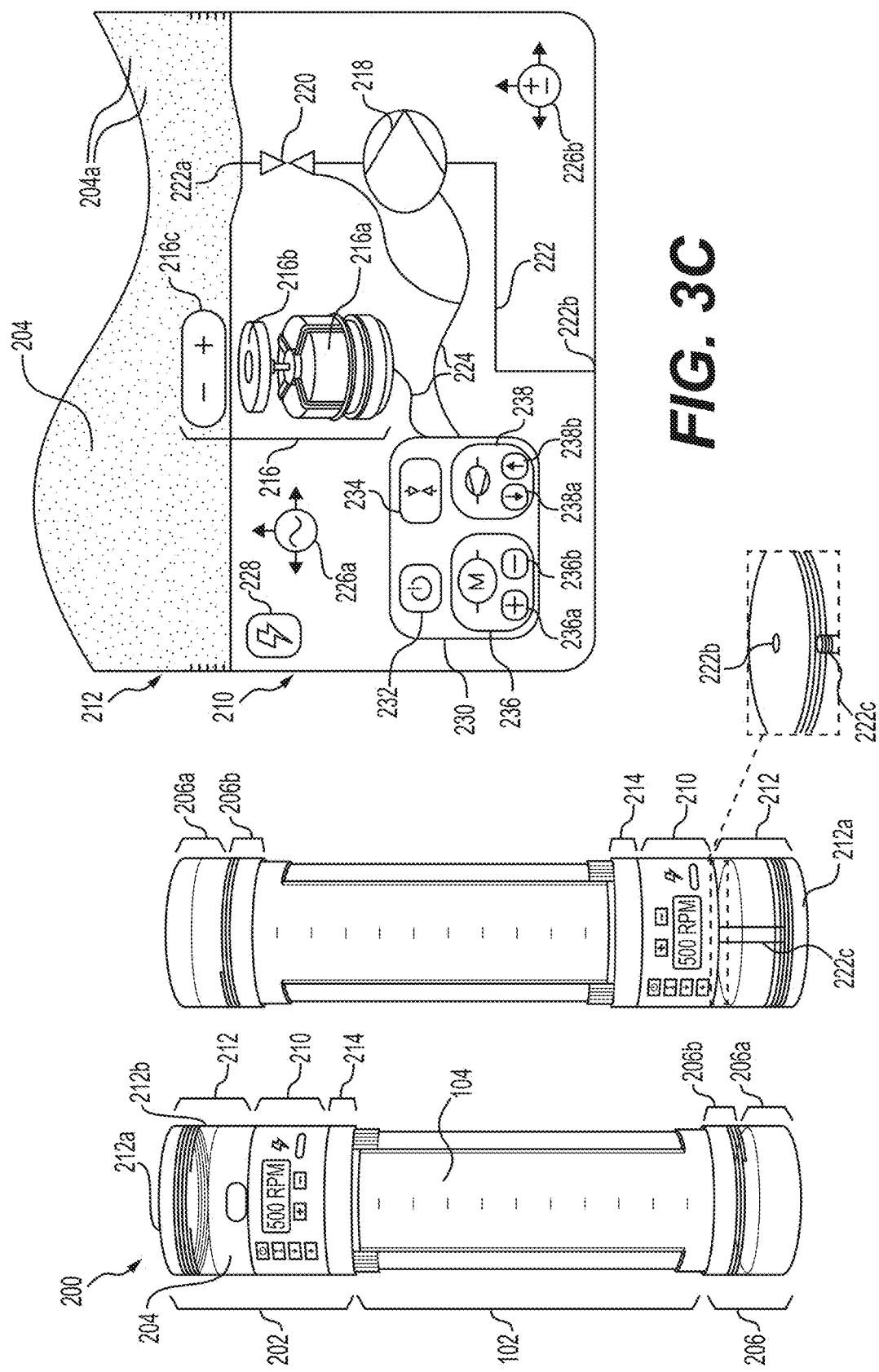

SOIL LAYER EXTRACTOR TOOL FOR SYSTEM OF OBSERVING SOIL SAMPLES

BACKGROUND OF THE INVENTION

Field of the Invention

The disclosure of the present patent application relates to soil and soil leachate testing, and particularly to a system using a common tube-shaped soil sampler for obtaining a soil sample, infusing the sample with leachate, and extracting different layers of the sample for analysis.

Description of Related Art

Soil sampling is a crucial practice for various reasons, impacting agriculture, environmental management, and landscaping. Soil samples can be used for determining the nutrient status of soils, allowing for precise and efficient fertilizer application and ensuring that crops receive the necessary nutrients for optimal growth, thereby leading to increased yields and cost savings for farmers. Soil samples can also be used for monitoring soil health through measurement of chemical, biological, and physical soil characteristics at different depths, thus providing vital information for maintaining soil fertility and ensuring sustainable agricultural practices. Furthermore, soil sampling can be used as an environmental protection scheme, where soil contamination is identified and managed in a suitable manner. Accurate soil data provides guidance towards better decision-making in crop management, landscaping, and construction. Soil samples allow for informative choices regarding planting, irrigation, and land use.

Soil is structured in distinct layers known as horizons. The arrangement of the different horizons from top to bottom are as follows: O Horizon (Organic Layer), A Horizon (Topsoil), B Horizon (Subsoil), C Horizon (Parent Material), R Horizon (Bedrock). Each of these horizons have its own specific characteristics.

One of the essential instruments used for soil sampling is the auger bucket. This tool is widely utilized in various fields such as agriculture, environmental studies, and construction. It is designed to collect disturbed soil samples from the surface or specific depths, providing valuable information on soil composition and quality. The auger bucket comes in different types, including standard augers for typical soils and specialized versions for sandy or compacted soils. Known for their durability and efficiency, auger buckets simplify the sampling process, allowing for faster and more accurate soil analysis. After collection, the soil sample undergoes different testing procedures, such as liquid (or nutrient) retention or dispersion. Liquid retention is performed by packing the soil column and then pouring liquid onto the as-packed sample. The soil leachate drained from the bottom of the sample is collected for further analysis after being monitored with respect to time and volume leaked. In addition, the subjected soil layers can also be separately analyzed to gain further insight on the effect of the employed liquid on the characteristics of the different layers and physical stability.

Suspensions, which are liquids containing dispersed particles on the scale of micro and nano size, have been scientifically proven to improve soil characteristics. For example, suspensions can be used to enhance the soil moisture retention, availability of nutrients, structure, erosion reduction, and contaminant remediation. However, testing suspensions on soils is currently done by moving the soil sample collected via an auger bucket tool to another container or sample holder. Such a method results in changing the soil structure, and thus demolishing the naturally existing passages within the sample. Moving the collected sample can also result in unintentionally mixing of the different vertical layers of the soil.

Thus, new systems and methods, solving the aforementioned problems, are desired for the extraction of a soil sample, dispensing of fluid and collection of leachate, and extraction of a soil sample.

SUMMARY OF THE INVENTION

The present disclosure is directed to a system for obtaining a soil sample, dispensing a liquid into the soil sample, collecting the resulting leachate, and extracting a soil layer from the obtained soil sample. The system includes a sample tube for obtaining and holding a soil sample, a fluid dispensing unit configured to attach to the sample tube and dispense liquid through the sample tube into the soil sample, and a collection unit configured to attach to the sample tube and collect leachate that has passed through the soil sample and the sample tube. A soil layer extraction tool is configured to hold the sample tube containing the soil sample, create an opening in the sample tube exposing the soil sample, and extract a layer of soil from the soil sample for analysis.

The sample tube for obtaining and holding a soil sample may include a removable section and a stationary section. The removable section of the sample tube includes a first vertical wall, a second vertical wall, and a top ring. The removable section fits within the stationary section in sliding relation thereto The top ring of the removable section is joined to upper edges of the first vertical wall and the second vertical wall. The stationary section has openings formed therein which are covered by the first vertical wall and second vertical wall of the removable section, when the removable section is inserted within the stationary section. The openings of the stationary section are exposed when the removable section is withdrawn from the stationary section. Stabilizing means are included on the stationary section for preventing rotation of the removable section within the stationary section. The stabilizing means may, for example, ribs on an inner surface of the stationary section. The ribs contacting sides of the first vertical wall and second vertical wall of the removable section.

A fluid dispensing and leachate collection system is provided that includes a fluid dispensing unit which may be cylindrical in shape and include a perforated disc therein as well as a bladed disc situated on top of the perforated disc. The bladed disc is rotatable on top of the perforated disc such that select patterns of perforations in the perforated disc are covered, or exposed, by rotation of the bladed disc. The fluid dispensing unit may contain a nanoparticle suspension which is dispensed into the sample tube and soil sample therein, and collected by a collection unit. A magnetic stirring system may be used to mix the nanoparticle suspension. A pump may be included in, or in connection with the fluid dispensing unit. The fluid dispensing unit includes a mating interface, such as threading, which allows coupling to a corresponding mating interface on the sample tube.

A soil layer extraction system includes a soil layer extractor tool having a base, a holder for a sample tube, and a crane for lifting walls of the sample tube to expose a soil sample held within the sample tube. The base may include a lower base portion, and an upper base portion joined in sliding relation to each other. A plurality of vertical posts may be mounted on the upper base portion, and a plurality of extractor blades may be mounted on the vertical posts for extracting a soil layer. The position of the extractor blades may be adjusted along the vertical posts. The extractor blades may include a lower blade and an upper blade, and further include a vertical blade positioned between the lower blade and upper blade. A soil layer is extracted by the tool through a sliding movement of the upper base portion which pushes the extractor blades and vertical blade into the exposed soil sample and thus removes a soil layer from the soil sample contained in the sample tube.

Further provided herein by the present disclosure, is a method for collecting and observing soil leachate. The method includes extracting a soil sample from the ground using a sample tube, attaching a fluid dispenser to the top of the sample tube, and dispensing liquid into the sample tube and soil sample therein using the fluid dispenser. A leachate collector is attached to the bottom of the sample tube and leachate is collected that has passed through the soil sample using the leachate collector.

Further disclosed herein, is a soil sample tube and system of extracting a soil sample from the ground. The soil sample tube includes a tubular body having a stationary section and a removable section. The stationary section includes a pair of diametrically opposed openings formed therein which are covered by diametrically opposed walls of the removable section. The diametrically opposed walls of the removable section are joined at upper edges thereof to a top ring. The removable section of the sample tube may fit within the stationary section, and the stationary section may include a plurality of flanges formed on an inner wall surface thereof. The plurality of flanges abut edges of the diametrically opposed walls of the removable section, and prevent rotation of the removable section when the removable section is inserted within the stationary section. The soil sample tube may include a top mating interface, such as threading, on a top opening thereof for placement of a fluid dispenser. The stationary section may be formed of transparent material and may include numbered graduations thereon. The removable section may be formed of metal.

The soil sample tube may be configured for coupling to a drilling head, and may include a bottom mating interface, such as threading, on a bottom opening thereof for attachment of the drilling head. In addition to the drilling head, a T-shaped handle may be included as part of the system for extracting a ground soil sample. The T-shaped handle may be attachable to the top mating interface of the sample tube. The T-shaped handle may include a cover having a bottom surface attachable to the top mating interface of the sample tube, and an elongated shaft threadedly engaged to a top surface of the cover.

A method of extracting a soil sample using the sample tube may include attaching a T-shaped handle to a top surface of a cover, attaching a bottom surface of the cover to a top opening of the sample tube, and attaching a drilling head to a bottom opening of the sample tube. The sample tube is inserted into the ground using the T-shaped handle to extract a soil sample from the ground into the sample tube.

In other embodiments, a soil leachate observation system is provided by the present disclosure. The soil leachate observation system includes a sample tube containing a soil sample therein, and a fluid dispenser configured to attach to the sample tube and dispense liquid into the sample tube and soil sample. The fluid dispenser includes a perforated disc with predetermined flow patterns, and a bladed disc situated on the perforated disc. The bladed disc is fixed in rotational arrangement on the perforated disc to selectively cover or expose the predetermined flow patterns. A fluid collector is configured to attach to the sample tube and collect liquid that has passed through the soil sample within the sample tube.

The fluid dispenser of the soil leachate observation system may include a nanoparticle suspension therein. The nanoparticle suspension is fed through the sample tube and soil sample therein and collected by the fluid collector. A magnetic stirrer may be included for mixing of the nanoparticle suspension prior to the suspension being dispensed into the soil sample. A pump may be included as part of, or in fluid connection with the fluid dispenser. The sample tube, fluid dispenser, and fluid collector may be directly attached by a mating interface such as a threaded connection.

In further embodiments, a method for observing soil leachate includes extracting a soil sample from the ground using a sample tube, the soil sample contained within the sample tube after being extracted from the ground, attaching a fluid dispenser to a top opening of the sample tube, and attaching a fluid collector to a bottom opening of the sample tube. A bladed disc is situated on top of a perforated disc within the fluid dispenser and is rotated to expose a predetermined flow pattern on the perforated disc. Fluid is dispensed from the fluid dispenser through the predetermined flow pattern of the perforated disc into the sample tube and soil sample. Leachate that has passed through the sample tube and soil sample is collected using the fluid collector. The perforated disc may include at least two or at least three predetermined flow patterns. The fluid dispensed from the fluid dispenser may be a nanoparticle suspension. The nanoparticle suspension may be mixed by a magnetic stirrer prior to being dispensed by the fluid dispenser. The method of observing soil leachate may include pumping the fluid into the soil sample of the sample tube. The method may include attaching the fluid dispenser and the fluid collector to the sample tube through a mating interface, such as a threaded connection.

In further embodiments, a system for soil layer extraction from a soil sample is provided by the present disclosure. The soil layer extraction system includes a sample tube containing a soil sample therein. The sample tube has first and second diametrically opposed openings exposing the soil sample therein. A soil layer extraction tool is included having a base and extractor blades including an upper blade, a lower blade, and a vertical blade mounted between the upper blade and lower blade. The upper blade is parallel to the lower blade, and the extractor blades are slidable in a parallel direction with respect to the base. The soil layer extraction tool includes a tube holder configured to hold the sample tube perpendicular to the base. The system includes positioning the sample tube within the tube holder and aligning the first and second diametrically opposed openings with the extractor blades such that the extractor blades are slidable into the soil sample. The sliding motion of the extractor blades into the soil sample results in a soil layer being extracted from the soil sample.

The soil layer extraction tool of the system includes a crane equipped with a winch and cable. The cable is attachable to the top ring of the sample tube whereby the removable section is retractable vertically by the winch from the sample tube. The winch includes a shaft on which the cable is wound, which may be connected to a manually operated crank lever. The winch may include a stop lever and a backward motion stopping gear. The backward motion stopping gear may be mounted on the shaft, and the stop lever may be movable between an open position disconnected from the stopping gear and a closed position in mating contact with the stopping gear. The closed position of the stopping gear prevents further rotation of the shaft.

The soil layer extraction tool may have a base including a lower base portion and an upper base portion connected by a rail on which the upper base portion is slidable in relation to the lower base portion. The extractor blades of the system may be mounted to the upper base portion using vertical posts. The lower blade portion of the extractor blades may include a pair of magnetic blades. The pair of magnetic blades includes a first magnetic blade and second magnetic blade, and the vertical blade of the extractor blades may be connected perpendicularly to the first magnetic blade and movable by a piston in sliding relation to the second magnetic blade.

In other embodiments, a method of extracting a soil layer includes extracting a soil sample from the ground using a sample tube, the sample tube containing the soil sample therein. Diametrically opposed openings in the sample tube are exposed to provide access to the soil sample. The method includes sliding extractor blades into the soil sample through the diametrically opposed openings. The extractor blades include an upper blade and a parallel lower blade connected perpendicularly to a vertical blade therebetween. The vertical blade pushes a soil layer out of the soil sample by the motion of the extractor blades into the soil sample. The method of extracting a soil layer may include placing the sample tube in a tube holder of a soil layer extractor tool. The method may include sliding an upper base portion relative to a lower base portion of the soil layer extractor tool, wherein the extractor blades are mounted to the upper base portion. The method may further include using a crane of the soil layer extractor tool to expose the diametrically opposed openings in the sample tube. The lower blade of the extractor blades may include a pair of magnetic blades. The pair of magnetic blades may include a first magnetic blade and a second magnetic blade, wherein a vertical blade is connected perpendicularly to the first magnetic blade and is movable by a piston in sliding relation to the second magnetic blade. The method may further include adjusting a vertical distance between the upper blade and the lower blade of the extractor blades. The vertical blade may be inserted between the upper blade and lower blade, the vertical blade being of predetermined size matching the vertical distance between the upper blade and the lower blade. In addition, a height of the vertical blade may be telescopically adjusted to equal the vertical distance between the upper blade and the lower blade.

These and other features of the present disclosure will become readily apparent upon further review of the following specification.

BRIEF DESCRIPTION OF DRAWINGS

FIG. 1A is a front view of a sample tube forming part of a system for soil extraction, leachate observation and soil layer extraction.

FIG. 1B is a front view of a fluid dispenser and fluid collector attached to a sample tube in a top-bottom and bottom-up configuration as part of a system for soil extraction, leachate observation and soil layer extraction.

FIG. 1C is a perspective view of a soil layer extractor tool forming part of a system for soil extraction, leachate observation and soil layer extraction.

FIG. 2A is a front view of a sample tube fitted with a T-shaped handle and a drilling head.

FIG. 2B is a front exploded view of a sample tube with T-shaped handle and drilling head.

FIG. 2C is an overhead perspective view of a mating connection between a T-shaped handle and sample tube.

FIG. 3A is a front view of a fluid dispenser and fluid collector arranged on a sample tube in a top-bottom configuration.

FIG. 3B is a front view of a fluid dispenser and fluid collector arranged on a sample tube in a bottom-up configuration.

FIG. 3C is a diagram representation of a reservoir portion and regulator portion of a fluid dispenser.

Similar reference characters denote corresponding features consistently throughout the attached drawings.

DETAILED DESCRIPTION

Figure 2D:
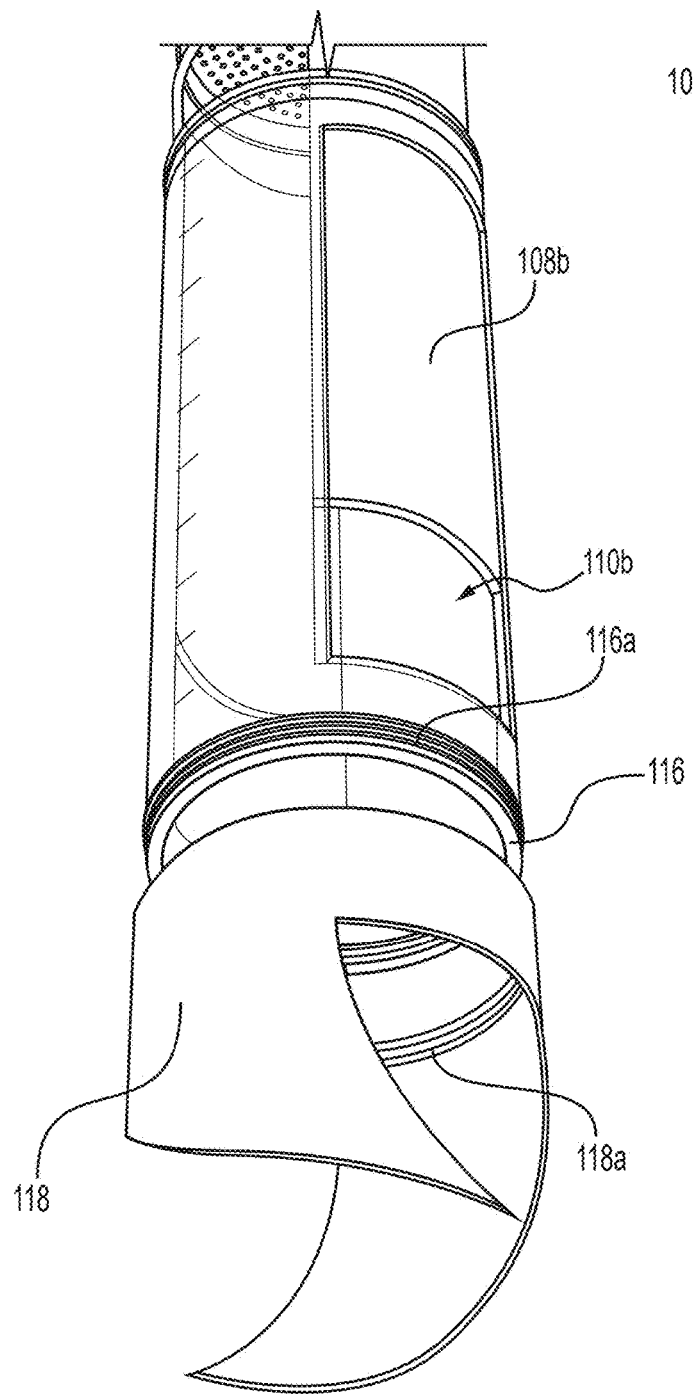
FIG. 2D is a bottom perspective view of a drilling head connection to a sample tube.
Figure 2E:
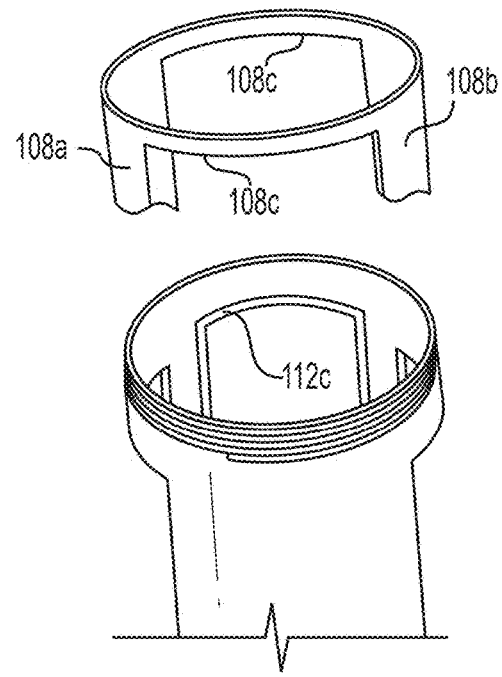
FIG. 2E is an overhead perspective view of a stationary section of a sample tube.
Figure 2F:
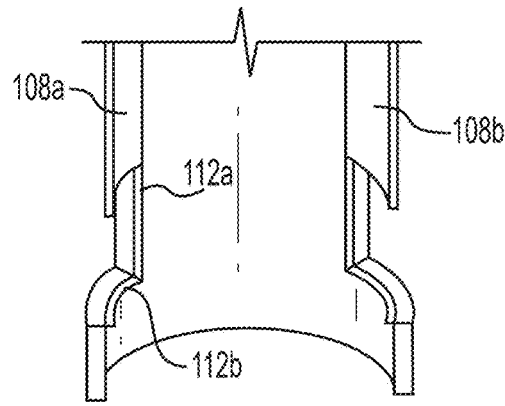
FIG. 2F is a front cutaway view of a bottom portion of a sample tube.

Referring to FIGS. 1A-C, the present disclosure is directed to an overall system 1 including subsystem 100 for extracting a soil sample, subsystem 200 for observing soil leachate, and subsystem 300 of extracting a soil layer from a soil sample. In reference to systems 100, 200, 300, these systems may be referred to in the present disclosure with terms such as "tools", "tool", "system" and "subsystem" interchangeably. Subsystem 100 of system 1 includes a sample tube 102 containing a soil sample 104 therein. A fluid dispensing unit 202 of subsystem 200 is configured to attach to a first end of the sample tube 102 and dispense liquid 204 through the first end of the sample tube 102 into the soil sample 104. A collection unit 206 is configured to attach to a second end of the sample tube 102 opposite the first end and collect leachate 208 that has passed through the soil sample 104 and the sample tube 102. System 200 for observing soil leachate may be arranged in a top-down configuration 200a or a bottom-up configuration 200b. A soil layer extraction tool 300 is configured to hold the sample tube 102 containing the soil sample 104 therein, create an opening 106 in the sample tube 102 exposing the soil sample 104, and extract a layer 104a of soil from the soil sample 104 for analysis.

Sample Tube and Soil Sample Extraction

Referring to FIGS. 2A-F, the sample tube 102 may include a removable section 108 and a stationary section 110, the removable section 108 including a first vertical wall 108a, a diametrically opposed second vertical wall 108b and a top ring 108c. The removable section 108 fits within the stationary section 110 in sliding relation thereto, and the top ring 108c is joined to upper edges of the first vertical wall 108a and the second vertical wall 108b. The stationary section 110 includes openings 110a, 110b formed therein which are covered by the first vertical wall 108a and second vertical wall 108b, respectively, of the removable section 108 when the removable section 108 is inserted within the stationary section 110. The openings 110a, 110b are exposed when the removable section 108 is withdrawn from the stationary section 110.

The removable section 108 of the sample tube may fit within the stationary section 110. The stationary section 110 may have a plurality of flanges 112a-c formed on an inner wall surface thereof. The plurality of flanges 112a-c abut edges of the diametrically opposed walls 108a, 108b of the removable section 108 and prevent rotation of the removable section 108 when inserted within the stationary section 110. Flanges 112a-c include vertical flanges 112a shown in FIG. 2F abutting vertical edges of first vertical wall 108a and second vertical wall 108b, and bottom flanges 112b which abut bottom edges of first vertical wall 108a, and second vertical wall 108b. Top flanges 112c shown in FIG. 2E abut the underside of top ring 108c.

The soil sample tube 102 may include a top mating interface 114a, such as threading, on a top opening 114 thereof for placement of the fluid dispenser 202 of FIG. 1. The stationary section 110 of sample tube 102 may be formed of transparent material and may include numbered graduations 111 thereon. The removable section 108 may be formed of metal such as stainless steel, aluminum, etc.

The soil sample tube 102 may be configured for coupling to a drilling head 118, and may include a bottom mating interface 116a, such as threading, on a bottom opening 116 thereof for attachment of the drilling head 118. The drilling head 118 is formed with corresponding threading 118a on an inner surface thereof. In addition to the drilling head 118, a T-shaped handle 120 may be included as part of the system 100 for extracting a ground soil sample 104. The T-shaped handle 120 may be attachable to the top mating interface 114a of the sample tube 102. The T-shaped handle 120 may include a cover 122 having a bottom surface attachable to the top mating interface 114a of the sample tube and an elongated shaft 120a threadedly engaged to a top surface 122b of the cover, such as through a male mating interface 122a. It should be understood, however, that the arrangement shown is a non-limiting example, and other coupling arrangements of the T-shaped handle may be provided, such as an integral formation of the T-shaped handle 120 and cover 122, or a mating interface in which T-shaped handle 120 is formed with a male threaded connection and cover 122 is formed with a female threaded connection, etc.

A disc 124 may be coupled to removable section 108 of sample tube 102, to facilitate vertical lifting of removable section 108 by a crane of a soil layer extraction tool, to be explained further on in the disclosure. Disc 124 may include perforations 124a of any size, shape, or quantity. The perforations 124a shown are non-limiting and disc 124 may instead be formed with open quadrants connected by arms, for example. Disc 124 may be coupled to removable section 108 by any suitable means including but not limited to a snap-fit connection between male members 124b formed in disc 124 and female openings 108d formed in removable section 108. Alternatively, screws and threaded openings may replace the snap-fit connection formed by male members 124b and female openings 108d. A snap-fit connection, however, is advantageous in that quick placement or removal of disc 124 onto removable section 108 is facilitated.

Disc 124, however, may be omitted altogether from removable section 108 if desired, as may be the case if soil sample 104 in sample tube 102 is to be treated with fluid for leachate observation. As such, disc 124 may be included or removed, as desired. A clasp or hook 124c may be formed on disc 124 to allow connection to a crane for lifting removable section 108, to be explained in further detail.

A method of extracting a soil sample using sample tube 102 includes attaching T-shaped handle 120 to a top surface 122b of cover 122, attaching bottom surface 122c of the cover 122 to top opening 114 of sample tube 102, the cover 122 having threading on an inner surface thereof corresponding to threading 114a of the sample tube 102. Drilling head 118 is attached to bottom opening 116 of the sample tube 102. The sample tube 102 equipped with drilling head 118 is inserted into the ground, using the T-shaped handle 120 attached thereto, the T-shaped handle is used to rotate the sample tube 102 and drilling head 118 thereby extracting a soil sample 104 from the ground into the sample tube 102.

Fluid Dispenser and Collector

Referring to FIGS. 3A-C, a soil leachate observation system 200 is provided by the present disclosure. The system 200 includes sample tube 102 containing soil sample 104 therein, and a fluid dispenser 202 configured to attach to the sample tube 102 and dispense liquid 204 into the sample tube 102 and soil sample 104. The fluid 204 dispensed from the fluid dispenser may contain nanoparticles or microparticles 204a and form a microparticle or nanoparticle suspension.

The reason behind using nano or macro particle suspensions is to increase the fertility of the soil, stabilize loose soil, increase the strength of soil aggregates by reducing wetting and swelling, enhance soil strength, reduce permeability, decrease the risk of liquefaction, improve soil compaction, reduce soil erosion, and improve the thermal conductivity of soils to benefit geothermal systems or underground cables. Examples of microparticles or nanoparticles 204a used to form the suspensions with the aim of improving the characteristics of soil include, but are not limited to, carbon-based materials (black carbon, carbon nanotubes, and graphene), metallic (Cu, Al, and Fe), metal oxides, organic (carbohydrates, nano-hydroxyapatite, and magnesium silicate).

The fluid 204 forming a nanoparticle suspension may be mixed by a magnetic stirrer 216 prior to being dispensed by the fluid dispenser 202. The inclusion of a magnetic stirrer is advantageous, as the nanoparticle suspensions may be formed within fluid dispenser 202 rather than having to produce the suspension externally and adding it to the fluid dispenser 202. It is to be noted that producing these nano or macro particle suspensions externally and placing them in a liquid dispensing container may cause changes to the fluid thermophysical properties due to the additional mixing caused from pouring the suspension into the container. Such changes in the thermophysical properties do not occur if the suspension is formed within the liquid dispensing container. Instead, the actual thermophysical properties of the formed suspension remain stable. Also, with the nanoparticle suspension being made within the liquid dispensing container, the physical stability of the suspension using an image capturing method over time may be observed, as the fluid dispenser would include a reservoir portion 212 of transparent material holding the nanoparticle suspension.

A pump 218 may be included for pumping fluid 204 into the soil sample 104 of the sample tube 102. In addition, although not shown, heating/cooling jackets may be used by the systems 100, 200, 300 disclosed herein, including application of external heating/cooling jackets on the sample tube 102 and the fluid dispenser 202.

Fluid collector 206 is divided into collection portion 206a and coupling portion 206b. Fluid dispenser 202 is divided into regulator portion 210, reservoir portion 212 and coupling portion 214. Reservoir portion 212 contains fluid 204 (i.e. nanoparticle suspension) to be dispensed into soil sample 104, and includes removable cap 212a coupled to sidewalls 212b, such as by a threaded connection.

In a non-limiting example, regulator portion 210 may include components, depicted diagrammatically, such as magnetic stirrer 216, pump 218, one or more valves 220, fluid conduits 222, electrical wiring 224, one or more power sources 226a, 226b, one or more charging ports 228, and electrical switches and controls 230. Such components, however, should be understood as non-limiting examples and some or all may be included in different combinations or omitted altogether. In its simplest form, for example, fluid dispenser 202 may include reservoir portion 212 directly attached to coupling portion 214 without the use of regulator portion 210, such as may be the case in which fluid 204 is a fluid other than a nanoparticle suspension, by way of example.

Shown in FIG. 3C, magnetic stirrer 216 may include components such as motor 216a, and magnetic disc 216b magnetically coupled to magnetized pellet 216c, magnetized pellet 216c rotating as a result of the rotation of magnetic disc 216b, such rotation resulting in the stirring of fluid 204. Power sources 226 may include AC power source 226a in connection with one or more DC power sources 226b, i.e. rechargeable batteries. A charging port 228 of any suitable kind such as USB, AC or any other type may be included on regulator portion 210.

Electrical controls 230 may include example switches/controls such as an on/off switch 232, valve opening/closing switch 234, magnetic stirrer control 236 and pump control 238. Magnetic stirrer control 236 may include motor speed increasing switch 236a, and motor speed decreasing switch 236b. Pump control 238 may include directional control switches 238a for downward flow, as in a top-down configuration and control switch 238b for upward flow, as in a bottom-up configuration. Pump 218 may be any suitable type including, but not limited to, a diaphragm, self-priming, axial, or any other pump type. In addition, pump 218 could be manually powered instead of electrically.

Similarly, the one or more valves 220 could be any suitable type such as a check valve, solenoid vale, or any other valve type. One or more valves 220 may be actuated manually and/or electrically. Fluid conduits 222 may be included in a suitable number and configuration and include an upper opening 222a from which fluid 204 enters regulator 210 in the top-down arrangement of FIGS. 3A, 3C. Upper opening 222a may be positioned within a slightly concave surface of regulator 210 to facilitate draining of fluid 204. Lower opening 222b is provided through which fluid 204 enters regulator 210 through pipe 222c in the case of a bottom-up configuration shown in FIG. 3B. Pipe 222c may be removably coupled to lower opening 222b, such as by threading. The bottom-up configuration of FIG. 3B is useful in that a bottom-up configuration can mimic natural groundwater movement, which typically flows upward through soil due to capillary action or in certain hydrological conditions. This approach helps predict how contaminants in groundwater could affect surface layers over time.

Figure 3D:
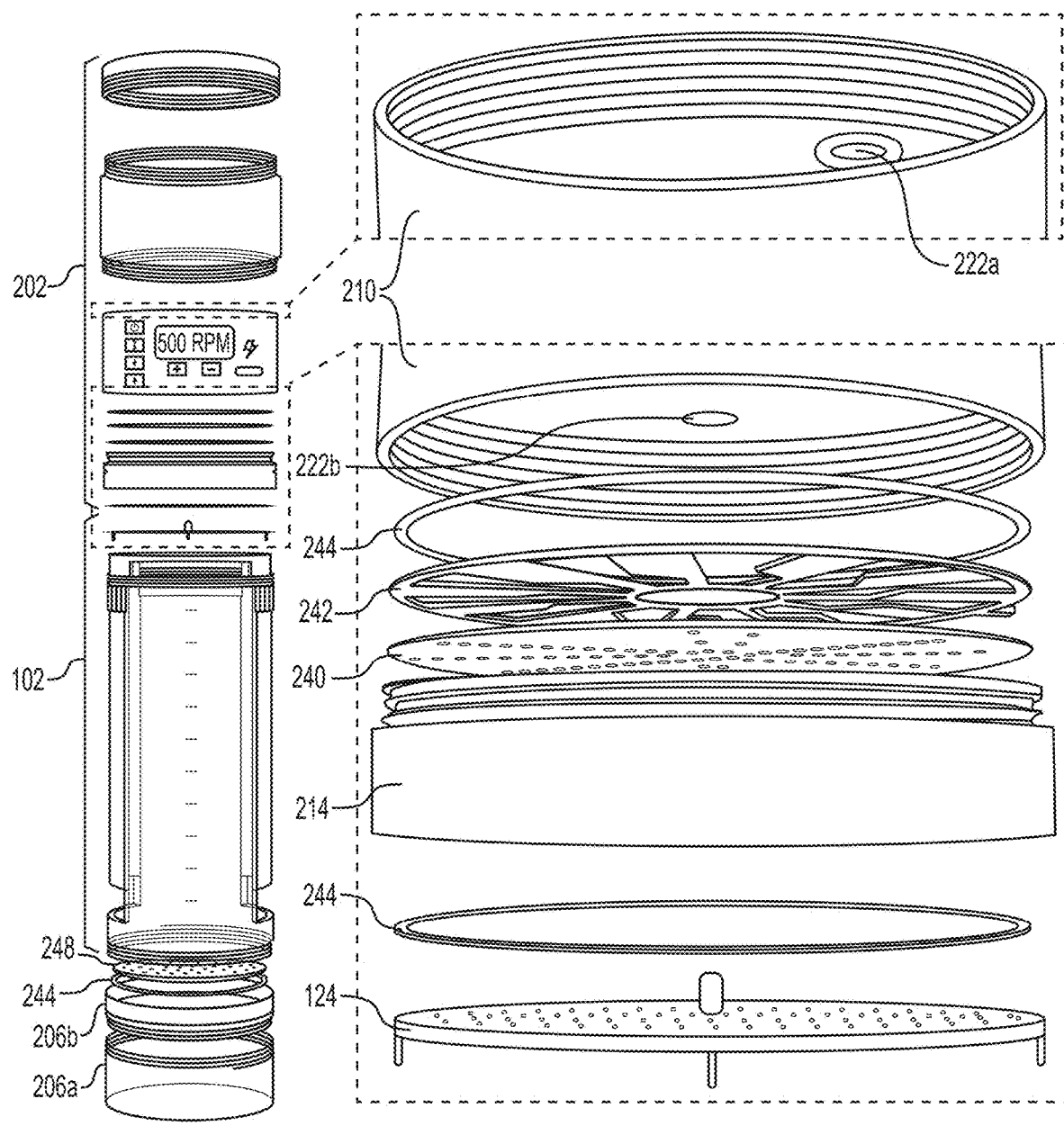
FIG. 3D is an exploded front view of a fluid dispenser, fluid collector and sample tube including closeup perspective views of portions of the fluid dispenser.
Figure 3E:
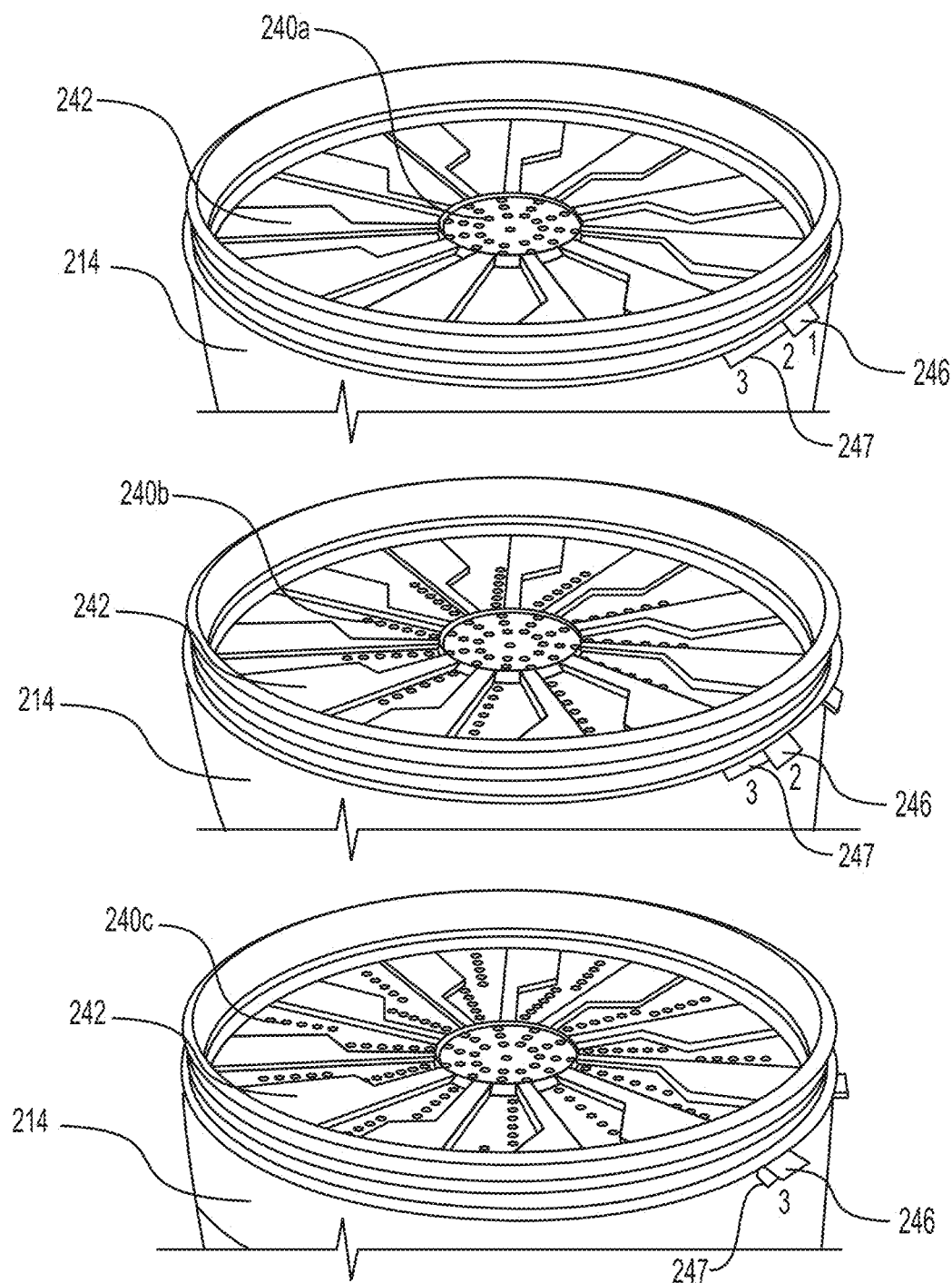
FIG. 3E is an overhead perspective view of flow arrangements provided by a perforated disc forming part of a fluid dispenser.

Referring to FIGS. 3D and 3E, the fluid dispenser 202 includes a perforated disc 240 with predetermined flow patterns 240a-c formed therein and a bladed disc 242 situated on perforated disc 240. The bladed disc 242 is fixed in rotational arrangement on the perforated disc 240 to selectively cover or expose the predetermined flow patterns 240a-c, including, as shown in FIG. 3E, low flow pattern 240a, medium flow pattern 240b, and high flow pattern 240c. The use of different flow rates and patterns is an important feature of system 200, allowing insights into how fluids and nutrients or contaminants move through the soil under various conditions. Different flow rates can influence how quickly nutrients/contaminants move through soil, impacting their spread in the environment. Faster flow rates can lead to quicker nutrient/contaminant dispersion, while slower rates may allow for more interaction between nutrients/contaminants and soil particles, potentially trapping contaminants in the soil. Flow rate studies help determine the permeability of different soil types, a key feature in applications such as agriculture, construction, and environmental remediation. High permeability means fluids (and potentially nutrients/contaminants) can move through the soil quickly, while low permeability can slow or restrict fluid movement.

A means may be included for rotating bladed disc 242 and selecting between the different flow patterns 240a-c. Means for rotating bladed disc 242 may be, for example, a tab 246 formed on bladed disc 242, which fits within a slot 247 formed in coupling portion 214. O-rings 244 may be included, as needed, for sealing purposes. For example, O-rings 244 may be situated between bladed disc 242 and regulator 210, and between disc 124 and coupling portion 214. Fluid collector 206 is configured to attach to the sample tube 102 and collect liquid that has passed through the soil sample within the sample tube. Fluid collector 206 may be equipped with mesh/perforated disc 248 and O-ring 244 between coupling portion 206b and sample tube 102.

Soil Layer Extraction

After applying fluid to the soil sample and collecting the leachate, it may be useful to observe a layer of soil in which leachate passed through in order to gain insights into soil properties such as pH, and nutrient/contaminant content. Examining a soil layer may help assess changes in soil health, which can impact plant growth, crop yield, and overall ecosystems. Observing a soil layer can also provide insights into the mobility of contaminants, showing how quickly or slowly different substances travel through the soil. Such information may be useful in assessing contamination spread and planning soil remediation or containment efforts.

Figure 4A:
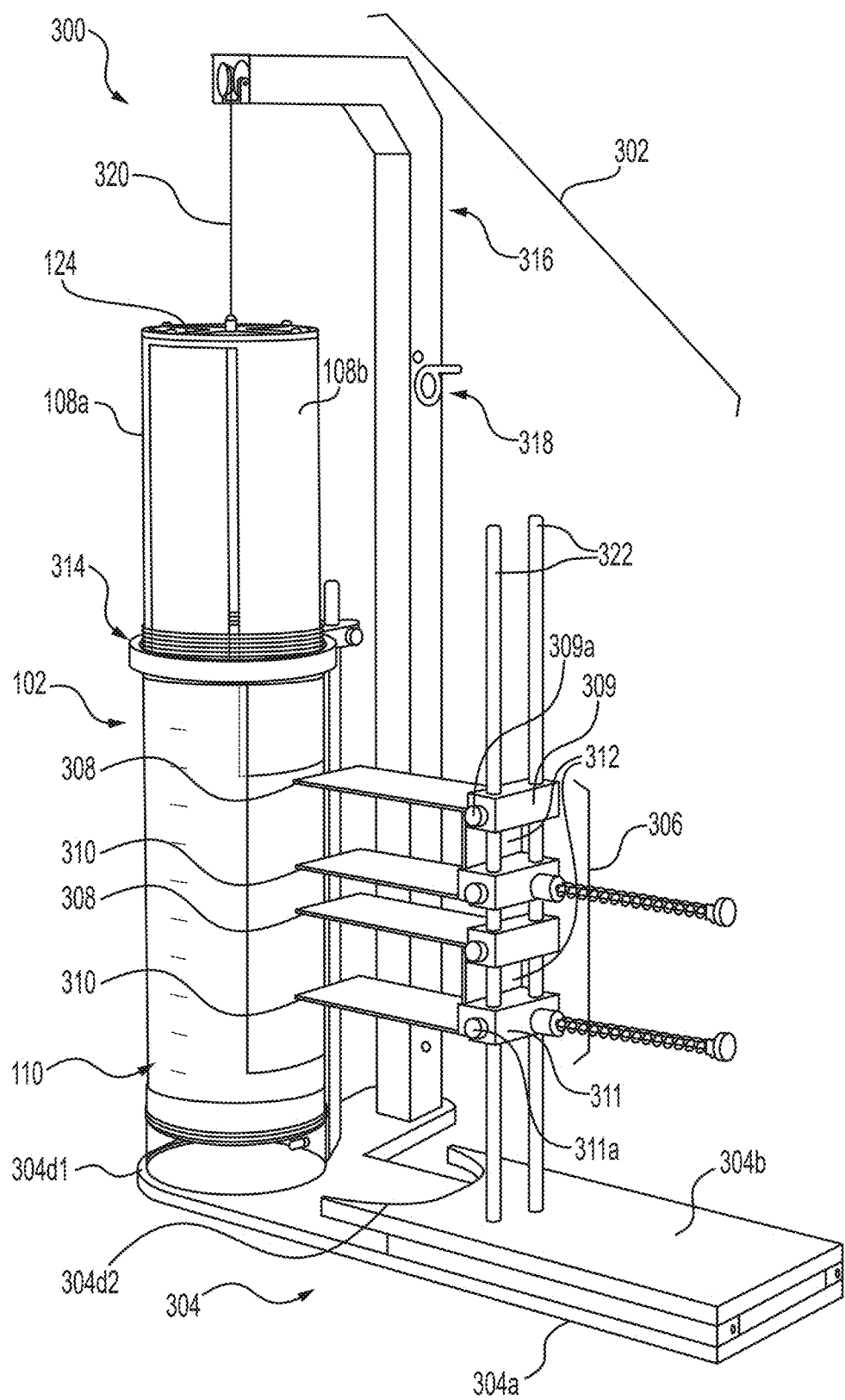
FIG. 4A is a perspective view of a soil layer extractor tool.
Figure 4B:
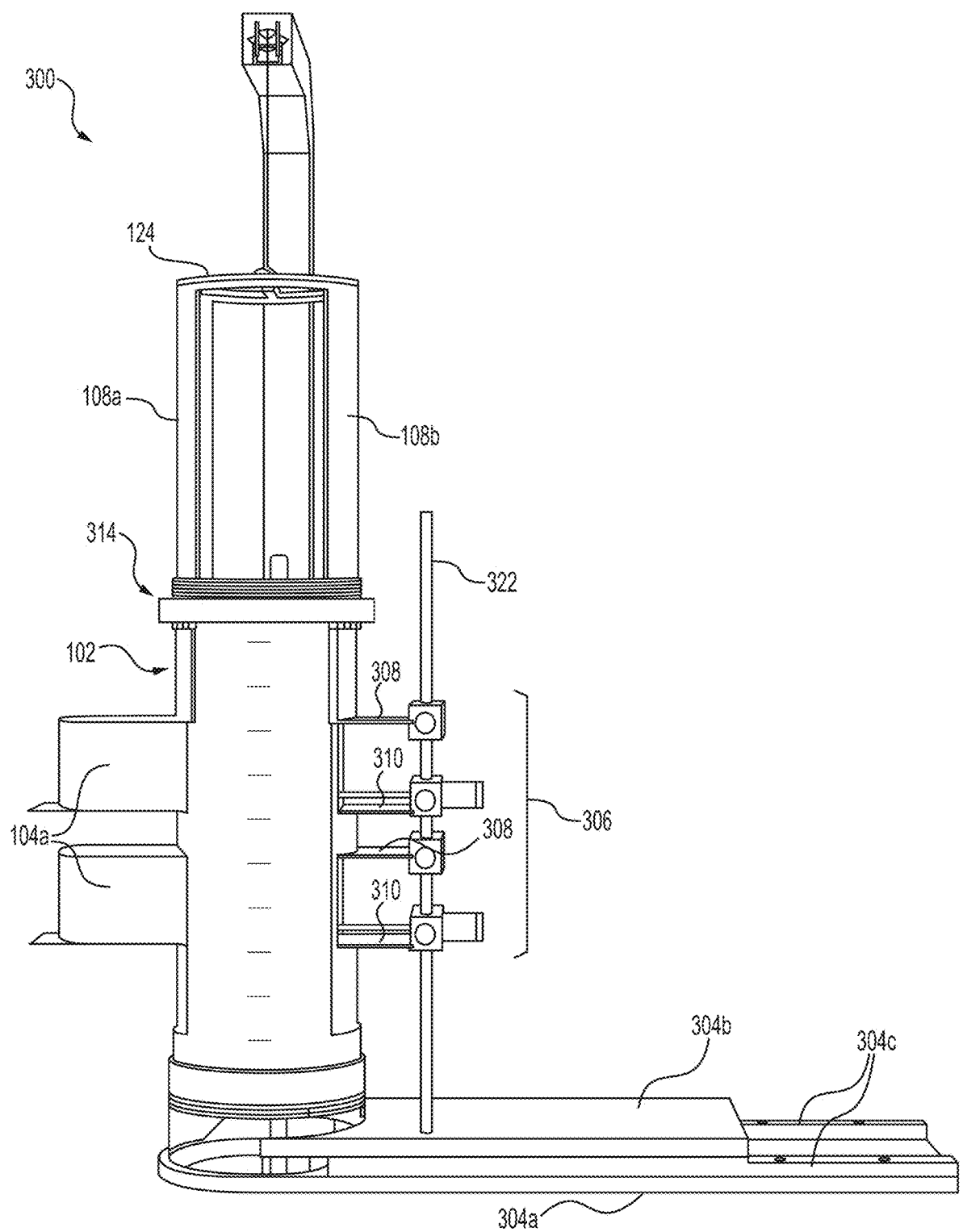
FIG. 4B is a perspective view of a soil layer extractor tool.
Figure 4C:
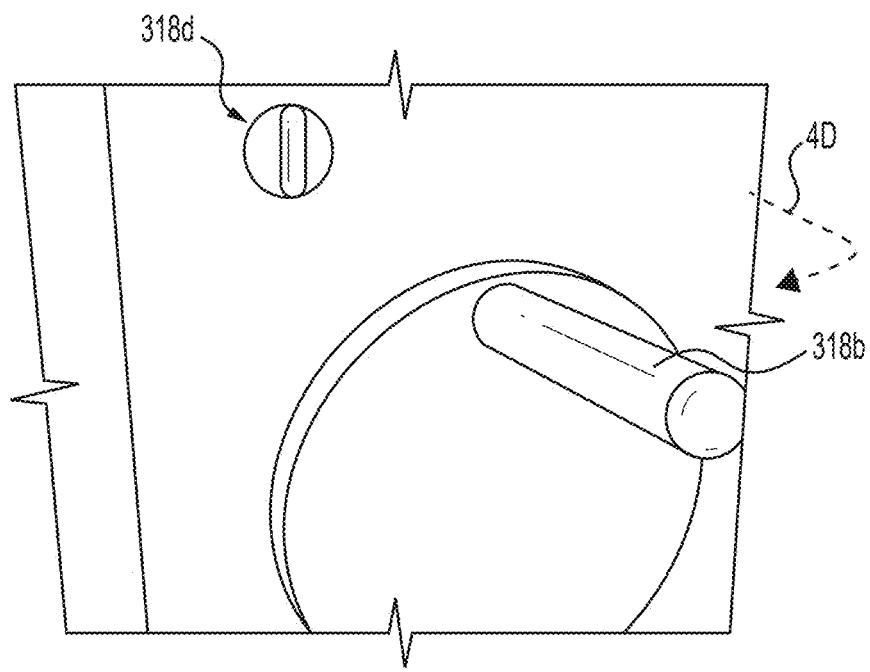
FIG. 4C is a perspective view of a crank forming part of a soil layer extractor tool.

Turning to FIGS. 4A-C, soil layer extraction system 300 is shown in greater detail. The soil layer extraction system 300 includes sample tube 102 containing a soil sample therein. A soil layer extraction tool 302 is included having a base 304 and extractor blades 306. Extractor blades 306 include upper blades 308 and lower blades 310 connected by vertical blades 312 mounted between the upper blades 308 and lower blades 310. Upper blade 308 is parallel to lower blade 310, and extractor blades 306 are slidable in a parallel direction with respect to base 304. The soil layer extraction tool 302 includes a tube holder 314 configured to hold sample tube 102 perpendicular to base 304. System 300 includes positioning sample tube 102 within tube holder 314 and aligning openings 110 in sample tube 102 with the extractor blades 306 such that the extractor blades 306 are slidable into the soil sample 104. The sliding motion of the extractor blades 306 into the soil sample 104 results in a soil layer 104a extracted from the soil sample 104.

Figure 4D:
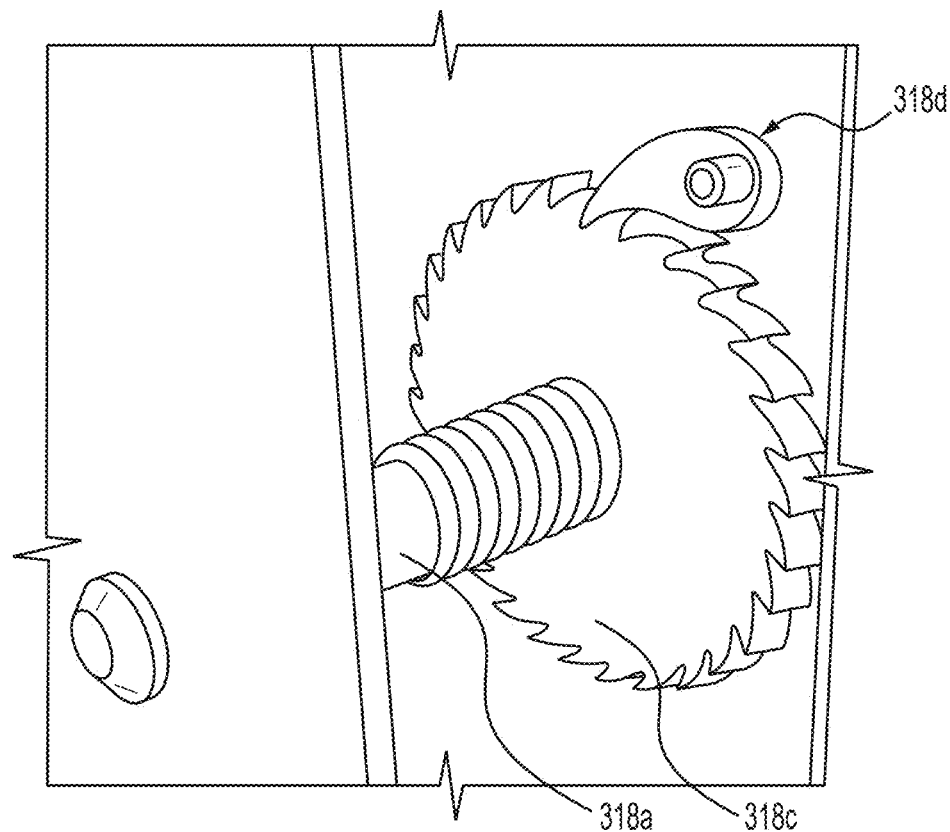
FIG. 4D is a perspective view of a winch shaft and gear forming part of a soil layer extractor tool.

The soil layer extraction tool 302 of the system includes a crane 316 equipped with a winch 318 and cable 320. Cable 320 is attachable to sample tube 102 via disc 124. Removable section 108 of sample tube 102 is retractable by the winch 318 vertically from sample tube 102. Winch 318 includes a shaft 318a on which the cable 320 is wound, which may be connected to a manually operated crank lever 318b, shown in FIG. 4C. Winch 318 may include a stop lever 318d and a backward motion stopping gear 318c, shown in FIG. 4D. Backward motion stopping gear 318c may be mounted on shaft 318a, and stop lever 318d may be movable between an open position disconnected from stopping gear 318c and a closed position in mating contact with stopping gear 318c. The closed position of stopping gear 318c serves to prevent further rotation of shaft 318a.

Base 304 of the soil layer extraction tool may include a lower base portion 304a and upper base portion 304b on which extractor blades 306 are mounted. Upper base portion 304b and lower base portion 304a may be connected by rail 304c on which upper base portion 304b is slidable in relation to lower base portion 304a. Vertical posts 322 may be mounted on upper base portion 304b for holding the plurality of extractor blades 306 thereon. The position of extractor blades 306 may be adjusted along vertical posts 322. Mounting blocks 309, 311 may be used for holding blades 308, 310, respectively, on vertical posts 322. Mounting blocks 309, 311, shown in FIG. 4A, may be used for vertical position adjustment of blades 308, 310, by tightening or loosening screws 309a, 311a, respectively. A cutout 304d1, shown in FIG. 4A, may be formed in lower base portion 304a, sized to fit sample tube 102, as well as a cutout 304d2 formed in upper base portion 304b.

Figure 4E:
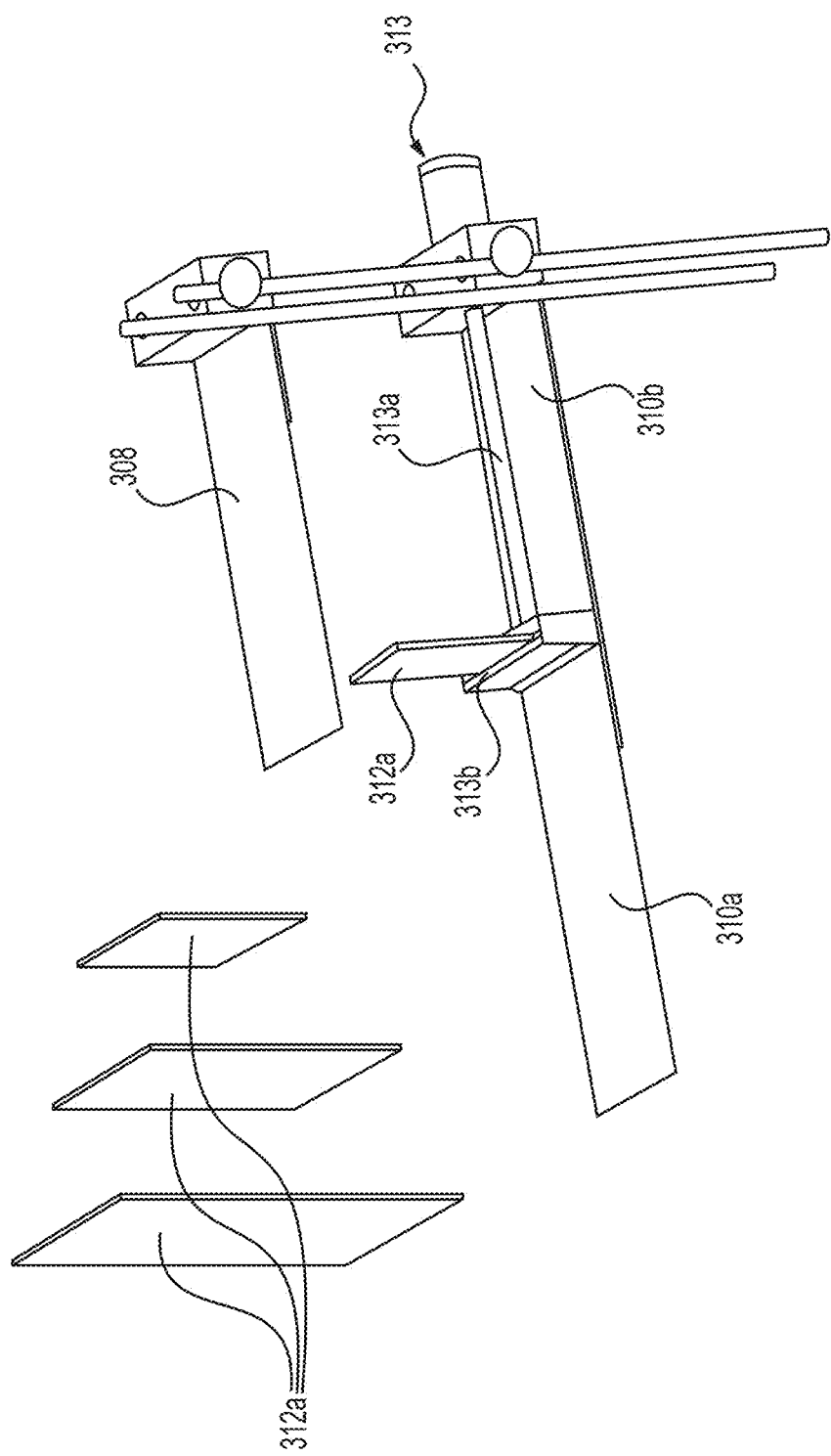
FIG. 4E is a perspective view of extractor blades using vertical blade inserts as part of a soil layer extractor tool.
Figure 4F:
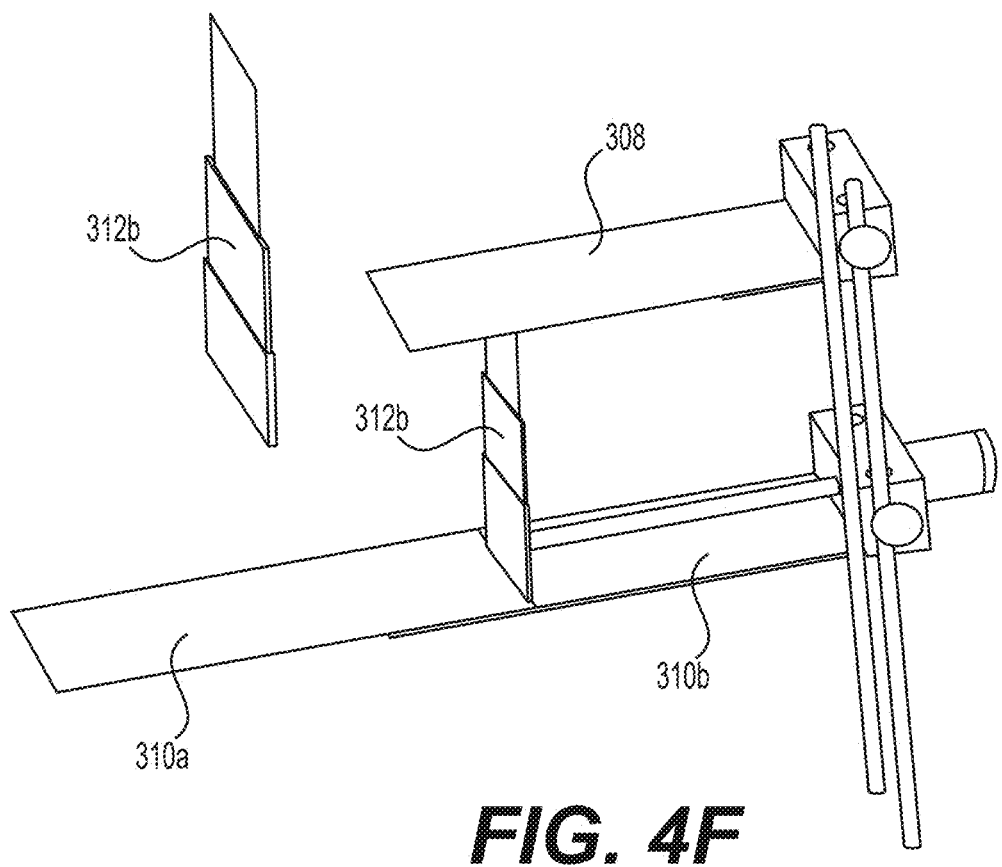
FIG. 4F is a perspective view of extractor blades using a telescoping vertical blade as part of a soil layer extractor tool.
Figure 4G:
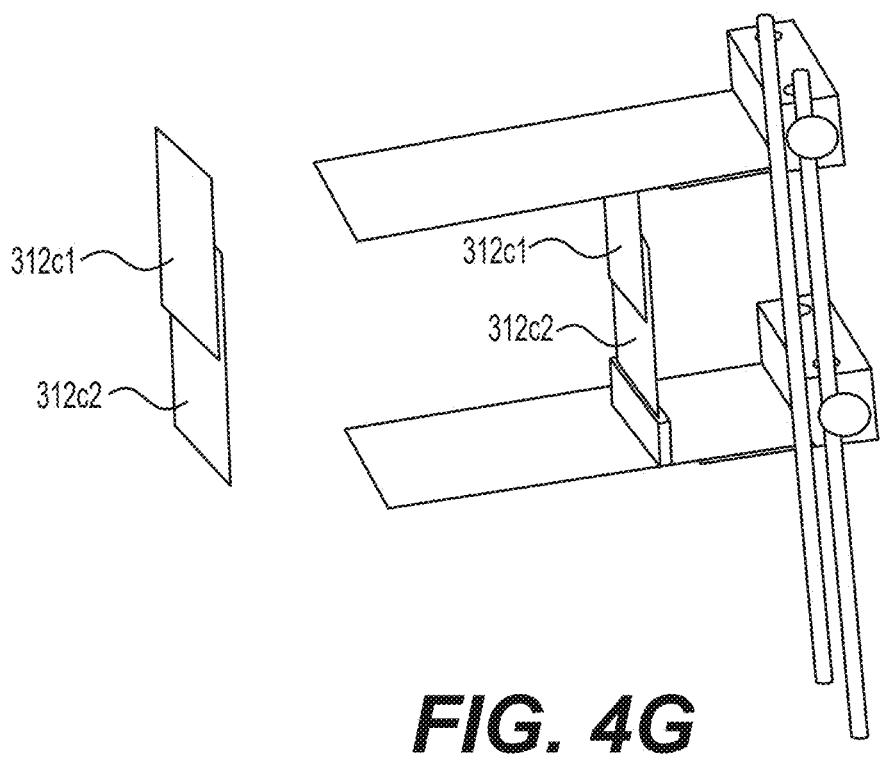
FIG. 4G is a perspective view of extractor blades using upper and lower vertical blade inserts as part of a soil layer extractor tool.

Turning to FIGS. 4E-4G, examples are given of various ways of arranging the vertical blade 312 between upper blade 308 and lower blade 310. In a non-limiting example, a pair of magnetic blades 310a, 310b may be included forming lower blade portion 310 of extractor blades 306. The pair of magnetic blades include first magnetic blade 310a and second magnetic blade 310b. In FIG. 4E, vertical blade 312 is connected perpendicularly to first magnetic blade 310a and is movable by piston 313 in sliding relation to second magnetic blade 310b. Blades 310a, 310b may be magnetic for stabilizing the positioning and orientation to relative to each other while still allowing for horizontal sliding through piston 313.

In the embodiment of FIG. 4E, vertical blades 312a are of predetermined size and are placed within slot 313b attached to shaft 313a of piston 313. In the embodiment of FIG. 4F, vertical blade 312b is telescopic by any suitable means, including a combination of springs and linear actuators, and automatically adjusts its height to match the distance between upper blade 308 and lower blade 310. In the embodiment of FIG. 4G, a pair of vertical blades 312c1 and 312c2 may be included on upper blade 308 and lower blade 310, respectively. The size of blades 312c1 and 312c2 is selected such as to allow for overlap between the blades, which are then positioned in close relation to effectively form a unitary wall pushing surface. Although piston 313 is included in the embodiments of FIG. 4G, 4E, it may be omitted, as in the embodiment of FIG. 4F, whereby the sliding motion of base 304 of cutting tool 302 pushes blades 308, 310 into the soil sample for extraction of a soil layer.

It is to be understood that the systems and methods disclosed herein are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A soil layer extraction system, comprising:
 a sample tube containing a soil sample therein, wherein the sample tube has first and second diametrically opposed openings exposing the soil sample therein;
 a soil layer extraction tool comprising:
  a base;
  extractor blades including an upper blade and a lower blade connected by a vertical blade mounted between the upper blade and lower blade, wherein the upper blade is parallel to the lower blade, and wherein the extractor blades are slidable in a direction parallel with respect to the base;
 a tube holder configured to hold the sample tube perpendicular to the base; and
 wherein the sample tube is positioned within the tube holder and the first and second diametrically opposed openings are aligned with the extractor blades such that the extractor blades are slidable into the soil sample within the sample tube thereby extracting a soil layer from the soil sample.

2. The soil layer extraction system as recited in claim 1, wherein the sample tube includes a removable section and a stationary section, wherein the first and second diametrically opposed openings are formed in the stationary section, and wherein the removable section includes a first vertical wall, a second vertical wall and a top ring, wherein the top ring is joined to upper edges of the first vertical wall and the second vertical wall, and wherein the removable section fits within the stationary section in sliding relation thereto.

3. The soil layer extraction system as recited in claim 2, wherein the soil layer extraction tool comprises a crane including a winch and cable, wherein the cable is attachable to the top ring and is retractable by the winch, thereby lifting the removable section vertically from the sample tube.

4. The soil layer extraction system as recited in claim 1, wherein the winch includes a shaft on which the cable is wound, the shaft connected to a manually operated crank lever.

5. The soil layer extraction system as recited in claim 4, wherein the winch includes a stop lever and a backward motion stopping gear, the backward motion stopping gear mounted on the shaft, and wherein the stop lever is configured to move between an open position disconnected from the stopping gear and a closed position in mating contact with the stopping gear, the closed position preventing rotation of the shaft.

6. The soil layer extraction system as recited in claim 1, wherein the base includes a lower base portion and an upper base portion on which the extractor blades are mounted, wherein the upper base portion and the lower base portion are connected by a rail on which the upper base portion is slidable in relation to the lower base portion.

7. The soil layer extraction system as recited in claim 1, wherein the lower blade includes a pair of magnetic blades, the pair of magnetic blades including a first magnetic blade and second magnetic blade, wherein vertical blade is connected perpendicularly to the first magnetic blade and is movable by a piston in sliding relation to the second magnetic blade.

8. A method of extracting a soil layer, comprising:
- extracting a soil sample from the ground using a sample tube whereby the sample tube contains the soil sample therein;
- exposing diametrically opposed openings in the sample tube, thereby providing access to the soil sample;
- sliding extractor blades into the soil sample through the diametrically opposed openings, the extractor blades including an upper blade and a lower blade, the upper blade and the lower blade being parallel to each other and connected perpendicularly to a vertical blade therebetween, wherein the vertical blade pushes a soil layer out of the soil sample by a sliding motion of the extractor blades into the soil sample.

9. The method of extracting a soil layer as recited in claim 8, further comprising placing the sample tube in a tube holder of a soil layer extractor tool.

10. The method of extracting a soil layer as recited in claim 9, further comprising sliding an upper base portion relative to a lower base portion of the soil layer extractor tool, wherein the extractor blades are mounted to the upper base portion.

11. The method of extracting a soil layer as recited in claim 10, wherein the soil extractor tool further comprises a crane and the diametrically opposed openings in the sample tube are exposed using the crane.

12. The method of extracting a soil layer as recited in claim 8, wherein the lower blade includes a pair of magnetic blades, the pair of magnetic blades including a first magnetic blade and second magnetic blade, wherein the vertical blade is connected perpendicularly to the first magnetic blade and is movable by a piston in sliding relation to the second magnetic blade.

13. The method of extracting a soil layer as recited in claim 8, further comprising adjusting a vertical distance between the upper blade and the lower blade.

14. The method of extracting a soil layer as recited in claim 13, further comprising inserting the vertical blade between the upper blade and lower blade, wherein the vertical blade is of predetermined size matching the vertical distance between the upper blade and the lower blade.

15. The method of extracting a soil layer as recited in claim 13, further comprising telescopically adjusting a height of the vertical blade to equal the vertical distance between the upper blade and the lower blade.

* * * * *